United States Patent [19]
Wickstrom et al.

[11] Patent Number: 5,958,775
[45] Date of Patent: Sep. 28, 1999

[54] COMPOSITION AND METHOD FOR TARGETED INTEGRATION INTO CELLS

[75] Inventors: Eric Wickstrom, Philadelphia; Stephen Cleaver, Hatfield, both of Pa.

[73] Assignee: Thomas Jefferson University, Philadelphia, Pa.

[21] Appl. No.: 09/121,527

[22] Filed: Jul. 23, 1998

Related U.S. Application Data

[60] Provisional application No. 60/054,146, Jul. 25, 1997.
[51] Int. Cl.[6] .......................... C12N 15/64; C12N 15/81; C12N 15/82; C12N 15/85
[52] U.S. Cl. ..................... 435/455; 435/320.1; 435/468; 435/473
[58] Field of Search .............................. 435/320.1, 172.3, 435/455, 468, 473

[56] References Cited

U.S. PATENT DOCUMENTS

| | | | |
|---|---|---|---|
| 4,590,162 | 5/1986 | Grinter et al. | 435/473 |
| 4,784,956 | 11/1988 | Grinter et al. | 435/473 |
| 5,102,797 | 4/1992 | Tucker et al. | 435/473 |

OTHER PUBLICATIONS

Rogers et al., Mol. Gen. Genet. 205:550–556 (1986).
Alton et al., "Non–invasive liposome–mediated gene delivery can correect the ion transprot defect in cystic firbrosis mutant mice", *Nature Genet.* 1993, 5, 135–142.
Arciszewska et al., Transposon Tn7 cis–Acting Sequences in Transposition and Transposition Immunity, *J. Mol. Biol.* 1989, 207, 35–52.
Arciszewska et al., Purification of TnsB, a Transposition Protein That Binds to the Ends of Tn7, *J. Biol. Chem.* 1991, 266, 21736–21744.
Arciszewska, L. and Craig, N.,"Interaction of the Tn7–encloded transposition protein TnsB witht he ends of the transposon", *Nuc. Acids Res.* 1991, 19, 5021–5029.
Bainton et al., "Tn7 Transposition: Target DNA Recognition Is Mediated by multiple Tn7–Encoded Proteins in a Purified In Vitro System", *Cell* 1993, 72, 931–943.
Chalfie et al., "Green Fluorsecent Protein as a marker for Gene Expression", *Science* 1994, 263, 802–805.
Chu et al., "Electroporation for the efficient transfection of mammalian cells with DNA", *Nucleic Acids Res.* 1987, 1311–1326.
Craig, N.L., Transposon Tn7, *Curr. Topics Micorbiol. Immunol.* 1996, 204 27–48.
Gamas, P. and Craig, N.L., "Purification and characterizationo f TnsC, a Tn7 transposition protein that binds ATP and DNA", *Nuc. Acids Res.* 1992, 20, 2525–2532.
Gargia–Buston et al., "Nuclear protein localization", *Biochim. Biophys. Acta* 1991, 1071, 83–101.
Gary et al., "Multiple DNA Processing Reactions Underlie Tn7 Transposition", *J. Mol. Biol.* 1996, 257, 301–316.
Hayward et al., "Activation of a cellular onc gene by promoter insertion in ALV–induced lymphoid leukosis", *Nature* 1981 290, 475–480.
Hyde et al., "Correction of the ion transport defect in cycstic fibrosis transgenic mice by gene therapy", *Nature* 1993, 362, 250–255.
Kotin et al., Site–specific integration by adeno–associated virus, *Proc. Natl. Acad. Sci. USA* 1990, 87, 2211–2215.
Kubo, K. and Craig, N., "Bacterial Transposon Tn7 Utilizes Two Different Classes of Target Sites", *J. Bacteriol.* 1990, 172, 2774–2778.
Lichtenstein, C. and Brenner, S., "Unique insertion site of Tn7 in the *E. Coli* chromosome", *Nature* 1982, 297, 601–603.
McKnight et al., "Molecular Cloning, cDNA Sequence, and Bacterial Expression of Human Glutamine:Fructose–6–phosphate Amidotransferase", *J. Biol. Chem.* 1992, 267, 25208–25212.
McKown et al., "Sequence Requirements of *Es herichia coli* attTn7, a Specific Site of Transposon Tn7 Insertion", *J. Bacteriol.* 1988, 170, 352–358.
Orle, K. Craig, N., "Identification of transposition proteins encoded by the bacterial transposon Tn7", *Gene* 1991, 104, 125–131.
Richards, T.C. and Greengard, O., "Distribution of Glutamine hexosephosphate Aminotransferase in Rat Tissues; Changes with State of Differentiation", *Biochim. Biophys. Acta* 1973, 304, 842–850.
Rothstein, R. *Methods of Enzymology*, vol. 194, Guide to Yeast Genetics and Molecular Biology, Academic Press, (1991) CHap. 19, 281–301.
Sayeski et al., "The murine glutamine:fructose–6–phosphate amidotransferase–encoding cDNA sequence", *Gene* 1994, 140, 289–190.
Waddel, C. and Craig, N.,"Tn7 transposition: Recognition of the attTn7 target sequenece", *Proc. Natl. Acad. Sci. USA* 1989, 86, 3958–3962.

*Primary Examiner*—Johnny F. Railey, II
*Attorney, Agent, or Firm*—Seidel, Gonda, Lavorgna & Monaco, PC

[57] ABSTRACT

A vector containing a selected nucleic acid sequence interposed between the terminal ends of a Tn7 transposon and a method for site specific integration of genetic material into a chromosome using those vectors are provided.

4 Claims, 3 Drawing Sheets

```
ProArgAsnLeuAlaAlaLysSerValThrValGlu***
H:CCACGGAATCTTGCCAAATCTGTGACTGTAGAGTAAGGAATATCTATACAAAATGTACGAAACTGTAT
    ||||||||| |||| || |||||| || |||||| ||  ||   |  
E:CCGCGTAACCTGGCAAATCGGTTACGGTTGAGTAATATATAGATGCCCTGCGTAAGCGGGGCATTTT
    || ||||  ||||| |||||| || |||| ||
Y:CCAAGAAACTTGGCTAAATCTGTTACCGTCGAATCAATTAACCCTTTTACTTTCTCTTCGTC
```

FIG. 1

COMPOSITION AND METHOD FOR TARGETED INTEGRATION INTO CELLS

CROSS-REFERENCE TO RELATED APPLICATION

This application claims priority from provisional application Ser. No. 60/054,146 filed Jul. 25, 1997.

REFERENCE TO GOVERNMENT GRANT

This invention was made in the course of research sponsored by the National Institutes of Health grant T32 CA09062. The U.S. Government may have certain rights in this invention.

FIELD OF THE INVENTION

This invention relates to the use of a modified transposon as a vector to deliver genetic material to the post-transcriptional termination region of a yeast, plant, animal, or human gene at a locus analogous to the attTn7 site of *Escherichia coli*.

BACKGROUND OF THE INVENTION

Although the potential of gene therapy is considerable, current applications have been limited by the available methods of delivery. No method has yet been identified which is able to produce a safe, targeted and efficient transfer of genetic material. Physical methods of cell delivery such as direct injection or liposome treatment deliver the therapeutic gene to the cell where it can be stably maintained extra-chromosomally for weeks to years depending on the cell type (Hyde et al. *Nature* 1993, 362, 250–255; Alton et al. *Nature Genet.* 1993, 5, 135–142). However, extensive monitoring and multiple administrations may be required for long term therapy via this method.

The use of engineered viruses, such as adenoviruses or retroviruses, as delivery and chromosomal integration systems takes advantage of the viral mechanisms to bind to target cells and incorporate DNA into chromosomes, thereby solving the multiple administration problem. These viral based integration systems target chromosomes in a nonspecific to region specific manner (Kotin et al. *Proc. Natl. Acad. Sci. USA* 1990, 87, 2211–2215). If the insertion occurs in random locations on the chromosome, the result could be the activation of a proto-oncogene or the disruption of a tumor suppressor gene, resulting in cell transformation. In retroviral based delivery vectors, the presence of the viral long terminal repeat (LTR), which has promoter and enhancer activities, can lead to inappropriate expression of downstream genes. This mechanism was studied in the activation of the proto-oncogene c-myc by an avian leukosis virus (ALV) infection (Hayward et al. *Nature* 1981 290, 475–480).

One possible method to avoid the transformation of a target cell is to design a system that allows for site-specific integration in an accessible but non-essential region of the target cell chromosome. In addition, the integrated DNA should have no enhancer or promoter effects on the surrounding genes.

The transposon Tn7 has the ability to perform site-specific recombination downstream of the bacterial glutamine synthetase (glmS) transcriptional terminator (Craig, N. L., *Curr. Topics Microbiol. Immunol.* 1996, 204 27–48; Gary et al. *J. Mol. Biol.* 1996, 257, 301–316). The transposed DNA has no obvious effects on the transcription of glmS or the next downstream gene phoS (Kubo, K. and Craig, N., *J. Bacteriol.* 1990, 172, 2774–2778; Waddel, C. and Craig, N., *Proc. Natl. Acad. Sci. USA* 1989, 86, 3958–3962; McKown et al. *J. Bacteriol.* 1988, 170, 352–358). The glmS gene has significant sequence identity to the human glutamine:fructose amidotransferase 6-phosphate (GFAT) and glutamine-fructose-6-phosphate transaminase (GFPT) genes of yeast, on chromosome XI (Cheret et al. *Yeast* 1993, 9, 1259–1265), mice (Sayeski et al. *Gene* 1994, 140, 289–190), and humans (McKnight et al. *J. Biol. Chem.* 1992, 267, 25208–25212). GFPT is a housekeeping gene that is expressed in all cells, is expressed at higher levels in dividing cells, and is expressed at highest levels in tumor cells, as exemplified by a study conducted in rats (Richards, T. C. and Greengard, O., *Biochim. Biophys. Acta* 1973, 304, 842–850).

Transposons are mobile genetic elements that have the ability to translocate to a variety of sites on both chromosomal and extra-chromosomal DNA. Although transposons can be divided into subgroups based on their transposition mechanism, they all have similar DNA element structures (Orle, K. and Craig, N., *Gene* 1991, 104, 125–131). Transposons in their simplest form carry at least two genes. Typically, one gene codes for an antibiotic resistance factor and the second gene encodes one or more transposases. The transposase is an enzyme responsible for the recognition of the transposon DNA element, the insertion site on the target DNA, and for catalyzing the transposition event.

Tn7 is a 14 kb transposon that encodes antibiotic resistance to trimethoprim, streptomycin and spectinomycin (Lichtenstein, C. and Brenner, S., *Nature* 1982, 297, 601–603). In addition to the antibiotic resistance gene, Tn7 encodes five transposases, tnsA-tnsE, which are responsible for the transposition event (Bainton et al. *Cell* 1993, 72, 931–943; Orle, K. and Craig, N. 1991, supra). TnsA, B, and C are the core transposase proteins responsible for the transposition event, while TnsD and TnsE provide specific and nonspecific target sequence recognition, respectively (Bainton, et al. 1993, supra).

TnsA is a 31,000 dalton protein whose exact role in transposition is unknown but has been implicated in target strand breakage and transposon insertion (Bainton et al. 1993, supra; Orle, K. and Craig, N. 1991, supra). TnsB is a 81,000 dalton protein that recognizes and binds the Tn7 ends (Arciszewska et al. *J. Biol Chem.* 1991, 266, 21736–21744; Orle. K. and Craig, N. 1991, supra. TnsC is a 63,000 dalton protein that binds DNA and ATP (Gamas, P. and Craig, N. L., *Nuc. Acids Res.* 1992, 20, 2525–2532. Although this protein binds ATP, hydrolysis does not appear to be necessary for the transposition event. The hydrolysis of ATP has been implicated in transposition immunity (Arciszewska et al. *J. Mol. Biol.* 1989, 207, 35–52). TnsD is a 59,000 dalton protein that specifically recognizes and binds the DNA sequence in the attTn7 region (Bainton et al. 1993, supra; Orle, K. and Craig, N. 1991, supra). TnsE is a 61,000 dalton protein that also binds target DNA with little sequence specificity (Bainton et al. 1993, supra; Kubo, K. and Craig, N. *J. Bacteriol.* 1990, 172, 2774–2778). On the basis of sequence analysis, it appears that the genes tnsA and tnsB are contained within one operon and tnsC-tnsE each contain their own regulatory regions.

Mobile genetic elements also carry additional terminal sequence elements that are required for transposition. The two end elements are 10 to 30 base pairs in length and are either identical or closely related sequences that form a pair of terminal inverted repeats. The end elements play at least two functional roles. They act as a sequence specific binding site for the transposase protein and they signal the end of the transposon DNA sequence. The extreme terminal Tn7 end structures contain 30 bp terminal inverted repeats which are necessary for transposition (Arciszewska et al. *J. Mol. Biol.* 1989, 207, 35–52).

In addition to the terminal inverted repeat, the Tn7 left end segment (Tn7L) contains three separate, highly related 30 bp binding sites for TnsB (Arciszewska, L. and Craig, N., *Nuc. Acids Res.* 1991, 19, 5021–5029). The Tn7 right end segment (Tn7R) contains four of these highly related 30 bp TnsB binding sites. This non-symmetric arrangement may be responsible for the directionality of Tn7 insertion. These sites are bound by TnsB in an orderly, but non-cooperative fashion. The Tn7L sites fill from the innermost site towards the left terminal end, while the Tn7R sites fill from the right terminal end.

Although transposons rely on a site-specific DNA binding protein to recognize the end inverted repeats, most elements show little target specificity, resulting in random insertion events in target DNA molecules. Transposon Tn7 is distinguished from other transposons by its ability to insert at high frequency and at a specific location in the *E. coil* chromosome. The insertion site, known as attTn7, is located between two genes: glmS, which encodes a protein involved in hexosamine biosynthesis, and phoS, which encodes a protein involved in phosphate transport. The insertion of Tn7 at this site occurs in a single orientation in a non-replicative manner, and does not appear to disrupt the function of either glmS or phoS (Kubo, K. and Craig, N., *J. Bacteriol.* 1990, 172, 2774–2778); Waddel, C. and Craig, N., *Proc. Natl. Acad. Sci. USA* 1989, 86, 3958–3962; McKnown et al., *J. Bacteriol.* 1988, 170, 352–358). The recognition-insertion site is characterized by a 30 base sequence that lies in the 3' end of glmS. The recognition sequence is followed by a 25 base spacer region that locates the five base pair insertion point downstream of the glmS transcriptional terminator. The insertion point itself does not appear to have any specific sequence requirements (Kubo, K. and Craig, N. 1990, supra; Waddel, C. and Craig, N. 1989, supra). Although Tn7 preferentially inserts at the attTn7 site, it can also insert at various other sites with little sequence identity with each other and the attTn7 region (Kubo, K. and Craig, N. 1990, supra; Waddel, C. and Craig, N. 1989, supra). The nonspecific mechanism of insertion appears to be dependent on TnsE.

It is now believed that the terminal ends of a Tn7 transposon can be employed as a vector to insert genetic material into a specific site in yeast, plant, animal, or human chromosomes without disrupting the regulation and expression of genes surrounding the insertion site.

SUMMARY OF THE INVENTION

An object of the invention is to provide a vector comprising each terminal end of a Tn7 transposon and a selected nucleic acid sequence interposed between said terminal ends.

The invention further comprises a method for site specific integration of genetic material into a chromosome which comprises the steps of (a) constructing a vector which contains each terminal end of a Tn7 transposon and a selected nucleic acid sequence interposed between said terminal ends; (b) binding said vector to TnsB; (c) complexing the vector and bound TnsB of step (b) with TnsA, TnsC, and TnsD; (d) introducing the complex of step (c) to a host cell; and (e) growing said host cells for sufficient generations and under suitable conditions for the inserted genetic material to integrate into the chromosome of the host cells.

DESCRIPTION OF THE FIGURES

FIG. 1 illustrates the sequence alignment of the 3' termini of the human (H), SEQ ID NO: 1, and yeast (Y), SEQ ID NO: 2, GFPT genes as compared with the recognition-insertion region of Tn7, attTn7, in the 3' termini of *E. coil* glmS (E), SEQ ID NO: 3. The human gene insertion site is indicated by xxxxxx. Also depicted in this Figure is a fragment of the deduced amino acid sequence (SEQ ID NO:4) encoded by the human sequence.

DETAILED DESCRIPTION OF THE INVENTION

Figure 2A:
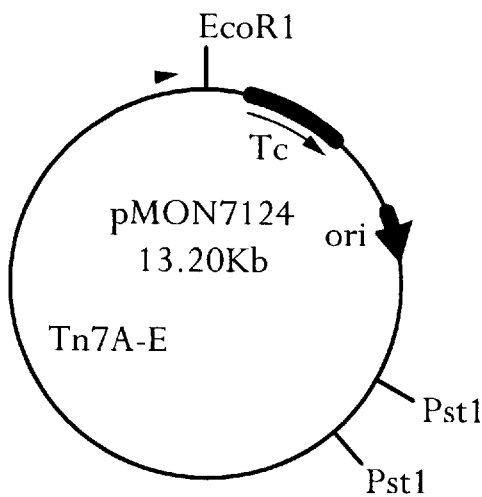
FIGS. 2A and 2B are schematics of the two plasmids used in the transpositional assay system. pMON-7124 (FIG. 2A) is the plasmid from which the transposon proteins were derived. pFasbac (FIG. 2B) is the plasmid which contains the gentamycin resistance marker flanked by the Tn7L and Tn7R ends and, serves as the DNA donor.

The invention is directed to a composition and a method for inserting genetic material into a specific designated site of a yeast, plant, animal, or human chromosome for safe, targeted and efficient transfer of genetic material.

The composition of the invention comprises a selected portion of a bacterial transposon to perform a site-specific insertion behind the coding region of a human housekeeping gene (GEPT) which is believed to be ubiquitous and continuously active. It has been found that the insertion into a site, analogous to the attTn7 insertion site of the *E. coil* chromosome, does not disrupt the regulation and expression of the surrounding genes.

A transposition recombination event is a three step process that is performed entirely by transposon encoded proteins (Bainton et al. *Cell* 1993, 72, 931–943). The first two steps generate a transposition intermediate and the third step resolves the insertion event. In the first step, the transposon DNA is recognized by a terminal inverted repeat structure and the DNA is cleaved at both ends, generating a pair of 3'-OH termini. Some transposable elements that transpose through a nonreplicative mechanism, such as Tn7, generate double stranded cuts at the ends of the transposon, while transposable elements that transpose through a replicative mechanism, such as phage Mu, generate only a single stranded cut.

The second step in the transposition recombination event, known as strand transfer, is the concerted cleavage of the target strand DNA coupled with the ligation of the transposon 3'-OH groups to the target DNA 5' phosphates to generate a recombination intermediate. The cleavage of the target DNA and the ligation event do not appear to be energetically coupled in that external sources of ATP are not required.

The third transposition step resolves the intermediate recombination structure. The type of processing required is dependent on the type of intermediate created. For the non-replicative elements, gap repair completes the process. In replicative transposition, the strand transfer intermediate is resolved by replication of the transposon, resulting in two copies of the transposon.

A tentative model has been proposed for Tn7 insertion based on binding assays and DNA footprinting (Arciszewska, L. and Craig, N., *Nuc. Acids Res.* 1991, 19, 5021–5029; Orle, K. and Craig, N., *Gene* 1991, 104, 125–131; Gamas, P. and Craig, N. L., *Nuc. Acids Res.* 1992, 20, 2525–2532; and Bainton et al. *Cell* 1993, 72, 931–943. There are three components of the proposed mechanism: target site recognition, Tn7 end element recognition, and the bridge. The specific or nonspecific target sites are bound by TnsD or E, respectively. Upon binding, a conformational shift is induced in these proteins, allowing TnsC to interact with TnsD or E and DNA in a non-specific manner. The Tn7 element ends are bound by TnsB. TnsB also interacts with TnsC, forming the bridge between the transposon DNA and the target site DNA. It has been suggested that TnsA then mediates the target strand breakage and insertion of the transposon into the *E. coil* chromosome (Bainton et al. 1993, supra). It has also been shown that Tn7 can transpose Tn7L and Tn7R ends that are trans of the location of the Tn7 proteins (Id.)

The glmS gene and the Tn7 insertion site have been cloned and sequenced (Waddel, C. and Craig, N., *Proc. Natl. Acad. Sci. USA* 1989, 86, 3958–3962; McKown et al. *J. Bacteriol.* 1988, 170, 352–358). The corresponding GFPT genes have been cloned and sequenced from yeast (Cheret et al. *Yeast* 1993, 9, 1259–1265), mice (Sayeski et al. *Gene* 1994, 140, 289–290), and humans (McKnight et al. *J. Biol Chem.* 1992, 267, 25208–25212). Overall, the *E. coli* gene and the human GFPT gene have 35% amino acid identity. FIG. 1 shows the sequence alignment of the human, *E. coli* and yeast GFPT 3' terminal regions.

The 3' terminal ends of the coding region for the *E. coli* and human genes share 73% nucleic acid identity, while the overall alignment has 49% identity. The nucleotides shown in bold for the *E. coli* 3' terminus have been determined to be important recognition sites for Tn7 (Kubo, K. and Craig, N., *J. Bacteriol.* 1990, 172, 2774–2778; Waddel, C. and Craig, N., *Proc. Natl. Acad. Sci. USA* 1989, 86, 3958–3962; McKown et al. *J. Bacteriol.* 1988, 170, 352–358). In a comparison of the conserved (bold) nucleotides within the coding region, the *E. coli* and human 3' terminal ends have 75% identity, while the overall alignment has 57% identity. The high degree of base conservation within the coding region, which is the binding site for TnsD, suggested that Tn7 could use the human GFPT sequence as a transposition target.

In the present invention, a vector is provided containing a portion of a Tn7 transposon to integrate genetic material into a yeast, plant, animal, or human GFPT gene. The vector is comprised of the terminal ends of the Tn7 transposon and a selected nucleic acid sequence interposed between the terminal ends. By "terminal end" is meant a sequence comprising approximately 100–200 bases from each end of the Tn7 transposon. In a preferred embodiment, the vector comprises approximately 100 bases from the left terminal end, and approximately 150 bases from the right terminal end. The selected nucleic acid sequence can be any sequence that encodes the protein of interest. The only limitation on the genetic material to be inserted is the size of the vector, which would include up to 14 Kb of genetic material, the size of Tn7. Based on sequence identity, the insertion of the vector into the host genome will be in the gene GFPT, at a site analogous to attTn7 in *E. coli*. The insertion site is illustrated in FIG. 1.

Figure 2B:
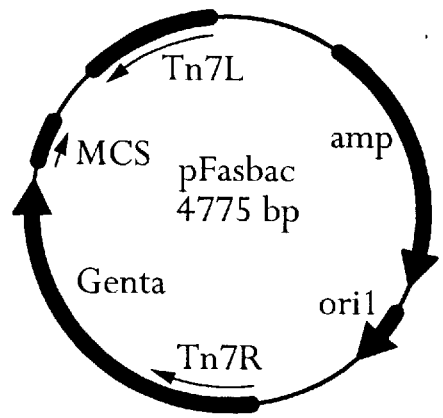

The vector of the present invention is derived from three plasmids, two of which contain the necessary components for transposition (FIG. 2A and 2B). Plasmid pMON7124 (Gibco-BRL) contains a tetracycline resistance marker and the five Tn7 genes that are responsible for catalyzing the transpositional event. The pFasbac (Gibco-BRL) plasmid contains a gentamycin resistance marker and a multiple cloning site within a 2.1 kb region flanked by the Tn7L and Tn7R ends. Because of the nonreplicative mechanism of Tn7 transposition, the pFasbac plasmid is lost from the cells in which transposition occurs. The third plasmid used to derive the vector contains a kanamycin resistance marker, and either the attTn7 target site or the proposed human target site. To test the ability of Tn7 to transpose into the target sites, the pMON7124 plasmid and the two target site plasmids were introduced and stably maintained together in *E. coli* JM109-DE3. The pFasbac plasmid was then introduced. The Tn7 proteins expressed by pMON7124 bind to the Tn7L and Tn7R ends on pFasbac and transpose the gentamycin resistance marker to the target site plasmids. This results in a 5.2 kb plasmid product that carries gentamycin and kanamycin resistance.

A method is also provided in the present invention for site specific integration of genetic material into a chromosome of a yeast, plant, animal, or human gene. The method comprises the steps of (1) constructing a vector which contains each terminal end of a Tn7 transposon and a selected nucleic acid sequence interposed between said terminal ends; (2) binding said vector to TnsB; (3) complexing the vector and bound TnsB of step (2) with TnsA, TnsC, and TnsD; (4) introducing the complex of step (3) to a host cell; and (5) growing said host cells for sufficient generations and under suitable conditions for the inserted genetic to pass into the chromosome of the host cells. The molar equivalent ratio of the complex of vector bound to TnsB is preferably at least seven to ten molar equivalents of TnsB to one molar equivalent of vector. The addition of TnsA, TnsC, and TnsD is to be carried under conditions such that at least one molar equivalent of each DNA binding protein is added per molar equivalent of vector. Preferably the molar equivalents of TnsA, TnsC, and TnsD are at least one to four. Introduction of the complex of step (3) to host cells may be carried out according to methods known to those of ordinary skill in the art including, but not limited to, electroporation, liposomal formulations, microinjection, or the use of a gene gun. Once the host cells have grown for sufficient cycles, assays such as Northern or Western blots may be carried out to determine the extent of mRNA or protein expression.

There are many potential therapeutic, agricultural and industrial applications for a site-specific gene therapy vector. In general, this system could be used to treat any type of disorder which would necessitate the stable expression of a therapeutic gene. This would include inheritable and non-heritable genetic disorders, as well as disorders caused by environmentally induced mutations. The use of the transposon as a gene therapy vector will only be limited by the understanding of the disease that needs to be treated. Several examples are discussed below in a nonexclusive list of problems which may be attributed to the loss of a particular gene function.

Cancer: A wide variety of modes of uncontrolled cell growth fall under the category of cancer. Solid tumors and leukemias exhibit mutational activation or overexpression of a family of proliferative genes. Cancer can also arise from the inactivation or underexpression of suppressor genes. In those instances where the malignant state is maintained by the underexpression of a suppressor gene, cell transformation may be reversed by the direct action of the gene product inserted by Tn7 mediated transposition. In malignancies caused by overexpression, the transformation could be reversed by the insertion of a gene coding for a repressor molecule, such as antisense RNA or a ribozyme.

Viral Infections: During viral infection of a cell, inhibitory proteins, or antisense RNA or ribozyme directed against viral-specific genes or gene products may prevent viral replication and production. Human immunodeficiency virus, rabies virus, herpes simplex virus, respiratory syncytial virus, and influenza virus are all candidates for this type of treatment.

Cardiovascular Diseases: Coronary artery bypass surgery, utilizing saphenous vein segments, often suffer from restenosis during the healing period right after surgery. Pretreatment of saphenous vein segments with a therapeutic gene for an antiproliferative protein, antisense RNA, or ribozyme, could reduce the extent and frequency of restenosis. A similar approach could be utilized during balloon angioplasty. In the case of familial hypercholesterolemia, a normal gene for the receptor for low density lipoprotein could be supplied to the liver by transposition, particularly by the liposome route, since liposomes concentrate in the liver.

Endocrinological Diseases: Elevated blood pressure results from abnormal levels of renin angiotensinase, or the precursor of vasopressin, depending on the individual involved. The transposon could be used to incorporate the gene for a therapeutic protein that reduces the production of these peptides, and could therefore improve the management of hypertension. Transposon-based gene therapy may also be of value in regulating the production of any other peptide hormone that is being underproduced or overproduced, inducing a variety of health problems.

Neurological Diseases: Alzheimer's disease may be due to genetic lesions in the gene for β-amyloid protein. The transposon could be used to deliver a normal copy of the gene for β-amyloid protein as well as an inhibitor for the mutant β-amyloid gene. This could reverse the effects of Alzheimer's disease.

Sickle Cell Anemia: Sickling of red blood cells in persons homozygous for sickle cell β-globin gene could be treated by introducing a normal copy of the β-globin gene into the chromosomes of hematopoietic stem cells.

Organ and Limb Regeneration: A variety of degenerative diseases destroy vital organs, such as the pancreas, liver, or kidney, and trauma may damage limbs beyond repair. The integration system could be used to deliver a gene for a developmental protein that would activate a regenerative pathway.

The transposon-based chromosomal integration system could also be applied in experimental applications where it would be useful to have the DNA of interest incorporated into the cell chromosome. Many of these applications could be predesigned and sold in a kit form.

Protein expression: Many proteins are toxic to the host bacterial cell when expressed at the high levels that are a characteristic of plasmid-based expression systems. The alternative is to use low copy number plasmids or mutations of the enhancer/promoter regions to suppress the level of expression. The transposon could be used to integrate the gene of interest into the bacterial chromosome. This would keep the copy number very low, and allow expression of the protein from the chromosome at the will of the investigator.

Polymerase: Bacteriophage T7 polymerase has many uses in molecular biology and protein expression. T7 polymerase is toxic to bacterial cells when expressed at high levels. This problem was solved by moving the T7 polymerase gene to the chromosome of several E. coli strains. Because T7 polymerase is used in many protein expression systems, it would be useful to create a construct that would allow the transposition of T7 polymerase to the chromosome of any bacterial strain. This would provide the scientific community with the ability to use T7 polymerase expression systems in a wide range of bacterial strains including mutated strains.

Chromosomal tracking: The transposon-based integration system could be used to transpose any type of reporter gene to the chromosome of a wide range of organisms. This would allow the parent chromosome to be traced through normal or aberrant cellular division. A similar system could be employed to study chromosomal damage and a wide variety of mutations.

Cancer research: Many of the transformed cell lines used as model systems contain several chromosomal mutations. In many cases, it remains to be determined whether several mutations or a single mutation is necessary for the transformation of a cell line. Using the transposon insertion system it would be possible to revert a single mutation at a time to determine the effects each mutation has on the transformation of the cell line.

Agriculture: In addition to site specific integration into yeast, animal, and human chromosomes, sequence identity with a number of plant species suggests that the modified Tn7 vector could be used for site specific integration into plants.

Plant species containing a number of sites with reasonable identity to the E. coli attTn7 sequence include *Amaranthus hypochondriacus, Anemia mexicana* (chloroplast), *Arabidopsis thaliana, Chara connivens* (chloroplast), *Marchantia polymorpha* (chloroplast), *Coleochaete orbicularis* (chloroplast), *Epifagus virginiana* (chloroplast), *Epichloe thyphina, Lycopersicon esculentum* (tomato), *Nicotinium tabacum* (tobacco), *Pisum sativum* (pea), *Sorghum vulgare, Triticum aestivum* (wheat), *Vigna unquiculata* (chloroplast), and *Zea mays* (corn).

The following examples are provided for illustrative purposes only and are not intended to limit the invention.

EXAMPLES

Example 1

Cloning of Target Plasmids

Figure 3A:
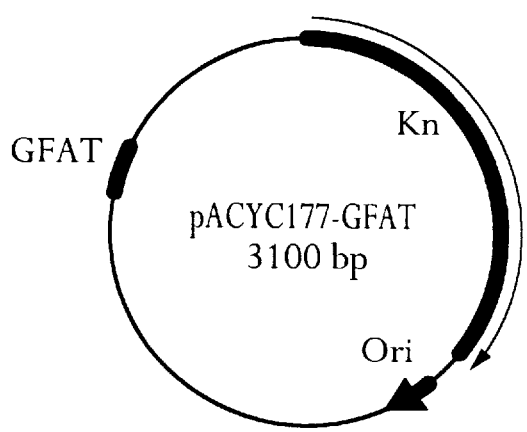
FIGS. 3A and 3B are the derived target constructs, pACYC177, used as the recipient plasmid for the transpositional event.
Figure 3B:
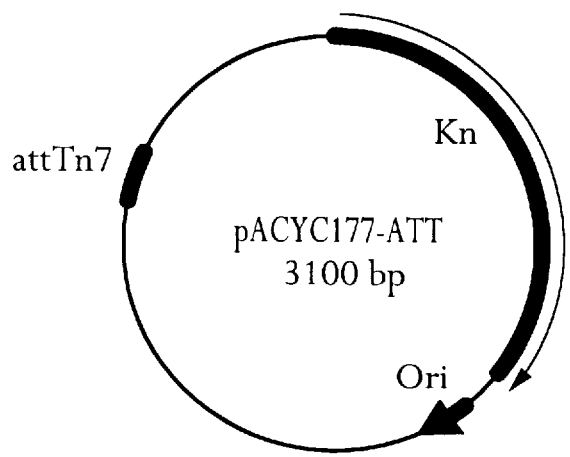

The attTn7 and the GFPT (GFAT) sequence and their complements were synthesized based on the sequence alignment (FIG. 1) and cloned into plasmid pACYC177 (New England Biolabs). Plasmid pACYC177 is a low copy number plasmid that contains a kanamycin resistance marker and the origin of replication from plasmid p15A that enables it to coexist with plasmids carrying the ColE1 origin of replication. This plasmid was chosen to carry the target sites to avoid plasmid incompatibility problems. The pACYC177 ligations were then transformed into E. coli strain JM109-DE3. The two plasmids, pACYC177-GFAT and pACYC177-attTn7 were then reisolated and sequenced to verify the insert. The target plasmids are shown in FIG. 3A and 3B.

Example 2

Determination of Target Site Activity

The plasmid pMON7124 containing the Tn7 TnsA-E genes responsible for catalyzing transposition was isolated from the E. coli strain DH10Bac (Gibco/BRL) and transformed into E. coli JM109-DE3. One culture, verified for the presence of pMON7124, was then made competent and split into three groups. One group was transformed with pACYC177-GFAT, another was transformed with pACYC177-attTn7, and the third group was transformed with the control plasmid pACYC177. All groups were then grown on dual selection kanamycin and tetracycline medium. The plasmids were reisolated from the positive colonies and verified by restriction digestion. One positive colony was then selected from each group and made competent. Each of the three groups was then transformed with plasmid pFasbac (FIG. 2B).

Figure 4:
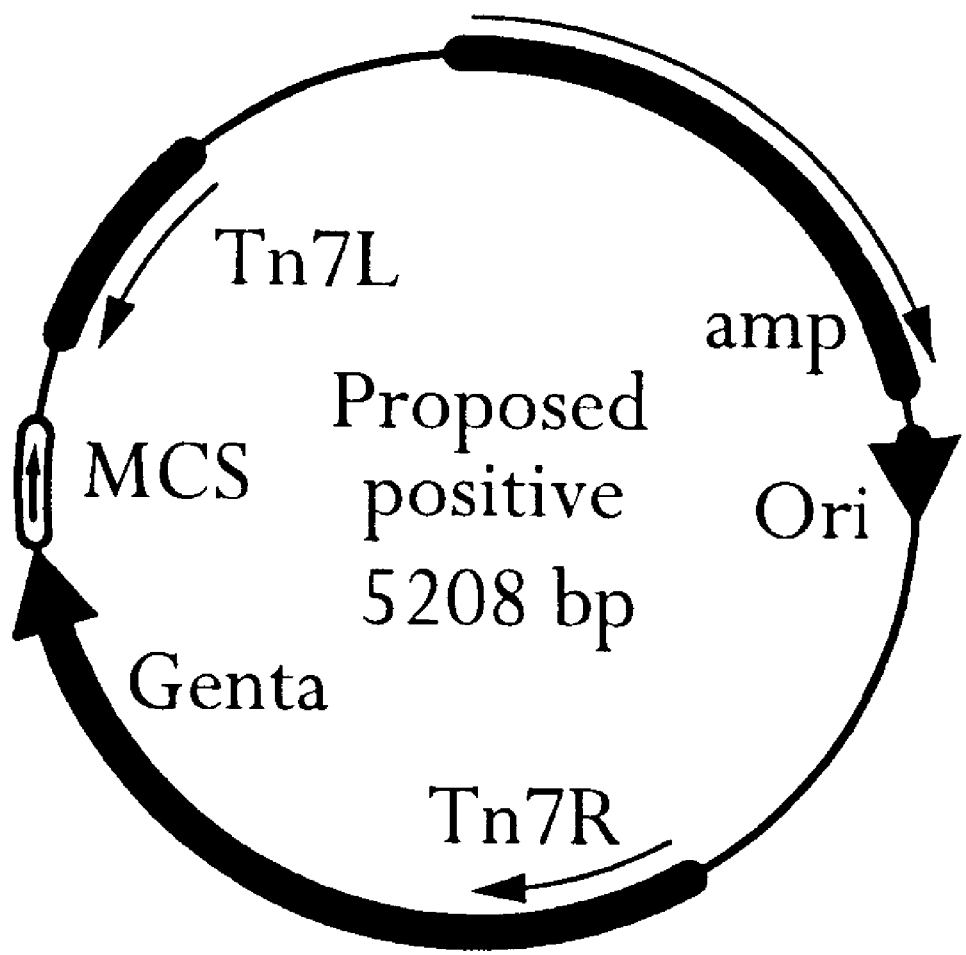
FIG. 4 is the 5.2 Kb positive plasmid generated by insertion of a 2.1 Kb fragment from pFasbac.

The transformants were grown for six hours in LB medium to allow transposition. The cultures were then plated on triple selective medium. There were four potential results of this experiment. If transposition did not occur, the result would be the maintenance of the three plasmids. Transposition could have occurred with only the chromosome as the target. This would have resulted in the loss of the pFasbac plasmid and the maintenance of the other two plasmids. If transposition occurs into the target or control plasmid, the result would be triple resistant colonies (tetracycline from pMON7124, kanamycin from the pACYC series, and gentamycin from pFasbac). In addition to triple resistance, transposition positive colonies would only contain two plasmids, pMON7124 and the 5.2 kb pACYC transposition product (FIG. 4).

The product plasmid represents the 3.1 kb pACYC177 plasmid with the 2.1 kb transposon insert. Transposition could also occur with the chromosome as a target; these cells would be triple resistant, and only contain the two plasmids, but the pACYC series plasmids would be the original size of 3.1 kb. Thirdly, if transposition did not occur, all three plasmids would be retained in the cell also resulting in triple resistant cells. Potentially, the transposition could occur to both the chromosome and the target plasmids; these cells would carry the triple resistance and have the larger pACYC series plasmids.

After transformation, two colonies were selected from each of the three pACYC target plates and the plasmids were reisolated. A mixed preparation representing all of the colonies from each of the plates was also prepared. A portion of each of the plasmid preparations was digested with BamH1 and resolved by gel electrophoresis. A second portion of the plasmid preparations was transformed into JM109-DE3 and plated on kanamycin/gentamycin plates. This combination of antibiotics selected for the 5.2 kb product while eliminating cells that transformed the pMON7124 or untargeted pACYC series plasmids. One colony was selected from each plate. The plasmids were reisolated, digested with BamH1, and resolved by gel electrophoresis.

There were no bands representing pFasbac in any of the experimental lanes, suggesting that transposition results in the loss of the pFasbac plasmid. The appearance of a 2.1 kb and a 3.1 kb band in the experimental lanes of the target site constructs demonstrates that both can be targeted for Tn7 transposition. In both constructs, the double resistance carried by the proposed positive plasmid was able to be transferred to and isolated from JM109. Although there were triple resistant colonies on the original pACYC177 plate, there was no transference of double resistance to JM109. The pACYC177 lanes of the gel do not show the 2.1 kb and 3.1 kb bands, suggesting that pACYC177 is not a target for Tn7 transposition.

The results of these experiments demonstrate that the modified transposon is active and is capable of transposing the gentamycin resistance marker into the chromosome of E. coli as well as the bacterial attTn7 and human GEPT sequences carried on plasmids. Thus, it is possible to transpose a gene of interest from a donor plasmid into the same human GFPT sequence on a human chromosome, as long as Tn7 TnsA-D proteins are supplied simultaneously. The simultaneous complexing of the TnsA-D could be achieved through the use of a liposome formulation.

Example 3

Transformation of Yeast Cells

Tn7 insertion within the target chromosomes of the simplest eukaryotic cells is confirmed in Saccharomyces cerevisiae cells permanently transformed with inducible tnsA-D. The cells are then transformed with a Tn7 vector to quantitate transpositional efficiency.

A yeast strain carrying separate tnsA,B,C,D under inducible promoters, GAL1-10 is generated in accordance with standard methods as taught by Rothstein, R. Methods of Enzymology, Vol. 194, Guide to Yeast Genetics and Molecular Biology, Academic Press, (1991) Chap. 19, 281–301. Into a yeast centromeric plasmid (YCp) construct carrying the GAL1-10 bidirectional promoter pair, with multiple insertion sites on either side, will be inserted tnsA on the GAL10 side, and tnsB on the GAL1 side. URA3, including its own promoter, is then inserted distal to tnsB, to allow for positive selection in a ura3 strain. Finally, a flanking upstream segment of leu2 is inserted distal to GAL10-tnsA, and a 3' flanking downstream segment of leu2 is inserted distal to GAL1-tnsB-URA3, yielding a plasmid YCpleu2::(tnsA, GAL1-10, tnsB, URA3) (YCp-tnsAB). The leu2::(tnsA, GAL1-10, tnsB, URA3) cassette is then excised, purified and used to transform S. cerevisiae Mat a, ade2-101, his3Δ200, trp1Δ63, ura3-52, which is plated on ura plates to select for the desired strain: Mat a, ade2-101, his3Δ200, leu::(tnsA, GAL1-10, tnsB, URA3), trp1Δ63, ura3-52. Disruption of the LEU2 gene is confirmed by PCR of genomic DNA. Similarly, a YCp lys2::(tnsC, GAL1-10, tnsD, HIS3) plasmid is constructed (YCp-tnsCD), the lys2::(tnsC, GAL1-10, tnsD, HIS3) cassette is excised, purified and used to transform S. cerevisiae Mat a, ade2-101, his3Δ200, leu2::(tnsA,GAL1l-10, tnsB, URA3), trp1Δ63, ura3-52, which is plated on his, ura plates to select for the desired strain: Mat a, ade2-101, trp1Δ63, his3Δ200, leu2::(tnsA, GAL1-10, tnsB, URA3), lys2::(tnsC, GAL1-10, tnsD, HIS3), trp1D63, ura3-52. As before, disruption of the LYS2 gene is confirmed by PCR of genomic DNA.

A Tn7 transposition donor plasmid is then constructed to insert SUP4 into the GFPT acceptor site, converting red S. cerevisiae ade2-101 colonies to white and allowing for quantitation of transpositional efficiency. A SUP4 gene is inserted into the Tn7 cassette of pFasbac; this Tn7-SUP4 cassette is then excised and inserted into a yeast integrative plasmid (YIp) construct (YIp-SUP4).

S. cerevisiae Mat a, ade2-101, trp1Δ63, his3Δ200, leu2::(tnsA, GAL1-10, tnsB, URA3), lys2::(tnsC, GAL1-10, tnsD, HIS3), trp1Δ63, ura3-52 are then induced to express the Tns proteins, made competent for transformation, then transformed with YIp-SUP11, or control plasmids lacking SUP4, or Tn7L/Tn7R ends, and plated on a his, ura medium supplemented with low levels of adenine, to yield some proportions of red and white colonies. White transposed colonies are picked for measurement of host cell GFPT to assess the effect of transposition on normal GFPT regulation and for identification of the site(s) of insertion by PCR of genomic DNA.

Alternatively, expression levels of Tns protein are measured by Western blot. If expression is low, inducer, adenine, and other medium components can be adjusted to maximize expression upon induction. If expression is satisfactory, then the Tn7 vector can be re-engineered into YCp with a LEU2 gene for positive selection on leu plates. Detectable white colonies in this mode require distinguishing between chromosomal transposition and maintenance of the transforming vector.

Example 4
Transformation of Mammalian Cells

In mammalian cells, purified Tn7 proteins are mixed with a Tn7 vector carrying an inducible reporter gene, then electroporated into murine NIH3T3 cells and human HL60 cells. Expression of the reporter gene is determined over time as a test for stable transformation. Sites of reporter gene insertion are determined by PCR sequencing. Expression of host cell GFPT is determined in the culture in accordance with procedures set forth in Example 2.

The Tn7 donor plasmid is constructed from pFasbac, without addition of a mammalian ARS or origin of replication, by excising the gentamicin resistance gene, and replacing it with β-galactosidase gene, excised from pβgal-Control (Clontech, Palo Alto, Calif.), or a green fluorescent protein gene such as that described by Chalfie et al. *Science* 1994, 263, 802–805 excised from the high fluorescence derivative pEGFP-C1 (Clontech, Palo Alto, Calif.) behind a strong constitutive promoter such as SV40 early or CMV immediate early, or a strong inducible promoter, such as MMTV. In *S. cerevisiae*, the remarkable high protease levels make it essential to transform host cells with inducible tnsA-D genes to ensure a plausible supply of transposition proteins to interact with the Tn7 donor plasmid. To simplify the task of transposition in mammalian cells, purified TnsA-D complexed with a Tn7 donor plasmid carrying a reporter gene are introduced into murine NIH3T3 fibroblasts and human HL60 promyelocytes by electroporation in accordance with procedures described by Chu et al. *Nucleic Acids Res.* 1987, 15, 1311–1326. Following introduction of Tns protein-DNA complexes into cytoplasm by this technique, trafficking into the nucleus should occur. Analysis of the amino acid sequences of TnsA-D revealed many segments which fulfilled the general requirements for nuclear localization signals taught by Garcia-Buston et al. *Biochim. Biophys. Acta* 1991, 1071, 83–101 to be "(1) typically short sequences, usually not more than 8–10 amino acids; (2) contain a high proportion of positively charges amino acids (Lys and Arg); (3) are not located at specific sites within the protein; (4) are not removed following localization; and (5) can occur more than once in a given protein."

Murine NIH3T3 cells are plated in DMEM with 10% FBS in 12.5 $cm^2$ flasks and allowed to attach and grow for two days in a humidified cell incubator with 5% $CO_2$ at 37° C., reaching 50–80% confluence, on the order of $10^6$ cells ($\approx 10^{-18}$ mole, 1 attomol) per flask. The cells are then trypsinized to release them; pelleted and washed once with fresh medium; resuspended in 0.5 ml of serum-free DMEM including approximately $10^{-15}$ mole (1 femtomol) Tn7 vector, 10 fmol TnsB, 5 fmol each TnsA, C, D; and electroporated in a cuvet of a BioRad Gene Pulser II, initially at 500 V/cm for 20 mseconds in accordance with procedures described by Chu et al. *Nucleic Acids Res.* 1987, 15, 1311–1326. Protein-vector amounts, electric field and pulse time are optimized for maximum cell survival and protein-vector uptake separately for each cell type. Electroporated cells are then plated in 65 mm culture dishes in medium containing X-gal, in the case of β-galactosidase, or normal medium in the case of green fluorescence protein, grown for two days, then observed microscopically to detect blue color (595 nm), or green fluorescence (excitation: 440 nm; emission: 510 nm) in individual cells, allowing quantitation of transpositional efficiency. The site(s) of insertion are identified by PCR of genomic DNA, and the impact of insertion on GFPT housekeeping expression is determined.

Human HL60 cells are inoculated into RPMI 1640 with 10% FBS; then grown in suspension in a humidified cell incubator with 5% $CO_2$ at 37° C. to a titer of $10^6$ cells/ml; pelleted and washed once with fresh medium; resuspended in 0.5 ml of serum-free RPMI 1640 with the same transposition components; and electroporated as described above. Electroporated cells are then inoculated into 65 mm culture dishes; grown for two days under the conditions set forth in the above paragraph; and observed microscopically.

What is claimed is:

1. A method for site specific integration of genetic material into a chromosome in a host cell at a site analogous to the attTn7 site of the *E. coli* chromosome, the method comprising the steps of:
   (a) constructing a vector which contains each terminal end of a Tn7 transposon and a selected nucleic acid sequence interposed between said terminal ends;
   (b) binding said vector to TnsB;
   (c) complexing the vector and bound TnsB of step (b) with TnsA, TnsC, TnsD;
   (d) introducing the complex of step (c) to a host cell; and
   (e) growing said host cells for sufficient generations and under suitable conditions for the inserted genetic to integrate into the chromosome of the host cell.

2. The method of claim 1 in which the site specific integration is in a yeast, plant, animal or human chromosome.

3. A complex comprising a vector which contains each terminal end of a Tn7 transposon and a selected nucleic acid sequence interposed between said terminal ends; and TnsA, TnsB, TnsC and TnsD complexed to said vector.

4. A complex according to claim 3 wherein the molar equivalent ratio of the vector
   (a) to TnsA is one to four;
   (b) to TnsB is seven to ten;
   (c) to TnsC is one to four; and
   (d) to TnsD is one to four.

* * * * *

SEQUENCE LISTING

<160> NUMBER OF SEQ ID NOS: 4

<210> SEQ ID NO 1
<211> LENGTH: 68
<212> TYPE: DNA
<213> ORGANISM: Homo sapiens

<400> SEQUENCE: 1
ccacggaatc ttgccaaatc tgtgactgta gagtaaggaa tatctataca aaatgtacga      60
aactgtat                                                              68

<210> SEQ ID NO 2
<211> LENGTH: 61
<212> TYPE: DNA
<213> ORGANISM: Saccharomyces cerevisiae

<400> SEQUENCE: 2
ccaagaaact tggctaaatc tgttaccgtc gaatcaatta accctttac tttctcttcg      60 t                                                                     61

<210> SEQ ID NO 3
<211> LENGTH: 68
<212> TYPE: DNA

```
<213> ORGANISM: Escherichia coli

<400> SEQUENCE: 3
ccgcgtaacc tggcaaaatc ggttacggtt gagtaatata tagatgccct gcgtaagcgg    60
ggcatttt                                                              68

<210> SEQ ID NO 4
<211> LENGTH: 11
<212> TYPE: PRT
<213> ORGANISM: Homo sapiens

<400> SEQUENCE: 4

Pro Arg Asn Leu Ala Lys Ser Val Thr Val Glu
 1               5                  10
```